United States Patent
Cioanta et al.

(10) Patent No.: US 7,014,652 B2
(45) Date of Patent: Mar. 21, 2006

(54) METHODS FOR TREATING PROSTATITIS

(75) Inventors: Iulian Cioanta, Weston, FL (US);
Richard Barry Klein, Cary, NC (US);
Jordan Dimitrakov, Brookline, MA (US)

(73) Assignee: ACMI Corporation, Southborough, MA (US)

( * ) Notice: Subject to any disclaimer, the term of this patent is extended or adjusted under 35 U.S.C. 154(b) by 55 days.

(21) Appl. No.: 10/763,856

(22) Filed: Jan. 22, 2004

(65) Prior Publication Data

US 2004/0172112 A1    Sep. 2, 2004

Related U.S. Application Data

(63) Continuation of application No. PCT/US02/24221, filed on Jul. 24, 2002.

(60) Provisional application No. 60/381,647, filed on May 17, 2002, provisional application No. 60/308,344, filed on Jul. 27, 2001.

(51) Int. Cl.
*A61F 7/00*    (2006.01)

(52) U.S. Cl. .................................... 607/105; 607/113
(58) Field of Classification Search ............... 607/96, 607/101–102, 113, 105
See application file for complete search history.

(56) References Cited

U.S. PATENT DOCUMENTS

| | | | |
|---|---|---|---|
| 4,423,725 A | 1/1984 | Baran et al. | |
| 5,084,044 A | 1/1992 | Quint | |
| 5,257,977 A | 11/1993 | Eshel | |
| 5,549,559 A | 8/1996 | Eshel | |
| 5,609,591 A | 3/1997 | Daikuzono | |
| 5,755,715 A * | 5/1998 | Stern et al. | 606/31 |
| 5,948,009 A | 9/1999 | Tu | |
| 6,136,020 A | 10/2000 | Faour | |
| 6,183,468 B1 * | 2/2001 | Swanson et al. | 606/40 |
| 6,216,703 B1 | 4/2001 | Manker et al. | |

* cited by examiner

*Primary Examiner*—Roy D. Gibson
(74) *Attorney, Agent, or Firm*—Ganz Law, P.C.

(57) ABSTRACT

Methods, systems, and computer program products for providing thermal therapies or internal thermal massage therapy for treating prostatitis by expanding and contracting a treatment balloon with inflation media and currently applying heat to a portion of the prostatic urethra.

49 Claims, 12 Drawing Sheets

Ø 1.0 cm ("L1") - up to 6.0 cm ("L2")

| Number of Patients | Baseline | | | Comments - 1 month | | | Comments - 3 months | | |
|---|---|---|---|---|---|---|---|---|---|
| | CPSI | | | CPSI | | | CPSI | | |
| | P | US | QL | P | US | QL | P | US | QL |
| 1 | 11 | 7 | 8 | 2 | 4 | 3 | 2 | 4 | 3 |
| 2 | 16 | 10 | 12 | 15 | 9 | 11 | 16 | 8 | 11 |
| 3 | 11 | 1 | 5 | 5 | 1 | 3 | 0 | 1 | 2 |
| 4 | 4 | 2 | 2 | 4 | 3 | 3 | 2 | 2 | 1 |
| 5 | 9 | 5 | 7 | 6 | 2 | 5 | 6 | 2 | 3 |
| 6 | 7 | 5 | 10 | 7 | 0 | 4 | | | |
| 7 | 8 | 6 | 8 | 4 | 5 | 3 | | | |
| 8 | 5 | 2 | 3 | 1 | 2 | 2 | | | |
| 9 | 3 | 4 | 6 | 2 | 0 | 1 | 2 | 1 | 1 |
| 10 | 9 | 2 | 7 | | | | | | |
| 11 | 9 | 4 | 7 | 11 | 4 | 7 | 10 | 4 | 6 |
| 12 | 10 | 6 | 10 | 8 | 2 | 5 | | | |
| 13 | 15 | 10 | 8 | 15 | 10 | 8 | | | |
| 14 | 14 | 0 | 9 | | | | | | |
| 15 | 18 | 7 | 9 | | | | | | |
| 16 | 15 | 4 | 11 | | | | | | |
| 17 | 3 | 0 | 1 | | | | | | |
| 18 | 13 | 0 | 10 | 14 | 0 | 10 | | | |
| 19 | 10 | 2 | 7 | | | | | | |
| 20 | 16 | 10 | 8 | | | | | | |
| Average: | 10.30 | 4.35 | 7.40 | 7.23 | 3.23 | 5.00 | 5.43 | 3.14 | 3.86 |

P = Pain      US = Urinary System      QL = Quality of Life

Figure 8

* Collected to date

METHODS FOR TREATING PROSTATITIS

RELATED APPLICATIONS

This application is a continuation of International Patent Application No. PCT/US02/24221, filed Jul. 24, 2002, which claims the benefit of and priority to U.S. Provisional Patent Application Ser. No. 60/308,344, filed Jul. 27, 2001 and U.S. Provisional Patent Application Ser. No. 60/381,647, filed May 17, 2002, the contents of which are hereby incorporated by reference as if recited in full herein.

FIELD OF THE INVENTION

The present invention is related to methods for treating prostatitis.

BACKGROUND OF THE INVENTION

It is believed that chronic prostatitis is one of the most common reasons why men visit urologists, even being characterized as the condition responsible for more outpatient visits than benign prostatic hypelplasia ("BPH") or prostate cancer. At least one report states that 35–50% of men will be affected by prostatitis at some time in their life. The treatments conventionally used to treat this condition have been generally problematic; most of the treatments have provided little hope that the condition could be predictably treated in a manner which could successfully alleviate the pain experienced by a large percentage of these individuals. Indeed, prostatitis has been termed "a waste basket of clinical ignorance" because of the lack of knowledge about the basic epidemiology of the disease and also the diagnosis and treatments available for same. See McNaughton Collins et al., *How Common is Prostatitis? A National Survey of Physician Visits*, Jnl. Of Urology, Vol. 159, pp. 1224–1228 (April 1998).

Unlike BPH, which occurs primarily in older men, prostatitis can occur in both younger (men in age groups of 18–50 (or younger)) and older men (over the age of 50), with the median reported patient age at about 40 years of age. *See How Common is Prostatitis?* supra at p. 1228. It is thought to be the most common urologic diagnosis for men less than 50 years of age.

There are several classifications or types of prostatitis, each of which may have different characteristics, manifestations, symptoms, or treatment protocols: Type I: acute bacterial prostatitis; Type II: chronic bacterial prostatitis; Type III: chronic (non-bacterial) prostatitis and/or chronic pelvic pain syndrome (CPPS); and Type IV: asymptomatic inflammatory prostatitis. See Nickel et al., *Research Guidelines for Chronic Prostatitis: Consensus Report From the First National Institutes of Health International Prostatitis Collaborative Network*, Urology, 54(2), pp. 229–233, 230 (1999).

The Type III prostatitis class (non-bacterial chronic prostatitis) is generally associated with urogenital pain in the absence of uropathogenic bacteria detected by standard microbiological methodology. See Nickel et al., *Research Guidelines for Chronic, supra*, p. 230. The Type III may be further defined as IIIA (inflammatory) or IIIB (noninflammatory). The IIIA inflammatory type prostatitis can be identified based on the presence of leulcocytes in expressed prostatic secretions or fluids, post prostatic massage urine, or semen, while the IIIB non-inflammatory type can be identified based on the absence of detectable leukocytes in similar specimens. This type of prostatitis may also be associated with variable voiding, sexual dysfunction, and/or psychologic alterations (particularly depression).

Only a small number of reported prostatitis cases are believed to be of the Type I or acute bacterial type, while the remaining classes of chronic prostatitis may affect an estimated 30 million men in the United States. In any event, as noted above, one of the primary symptoms of prostatitis is a chronic urogenital pain which can negatively impact the quality of life of individuals experiencing this condition. This pain may occur with urination, ejaculation, or in other urogential manifestations. It has been stated that the impact on the quality of life may be similar to those patients suffering unstable angina, a recent myocardial infarct, or active Crohn's disease. As such, chronic prostatitis is a major health care issue. See J. Curtis Nickel, *Prostatitis: Myth and Realities*, Urology 51 (3), pp. 362–366 (1998).

To assess the severity of prostatitis symptoms and responsiveness to certain therapies, certain standardized assessment protocols can be used. For example, the NIH Chronic Prostatitis Symptom Index (NIH-CPSI) uses a survey with nine questions and answers having assigned numerical weights so that a subject rate his degree of pain, the degree of symptoms, and his quality of life relating thereto. In this survey, the total of items 1a, 1b, 1c, 1d, 2a, 2b, 3, and 4 relates to the degree of the subject's pain, the total of items 5 and 6 relates to the degree of the urinary symptoms that the subject is experiencing, and the total of items 7, 8, and 9 relates to the subject's quality of life. Similarly, other scores, indexes and surveys can be used to diagnose or assess treatment efficacy, such as an International Prostate Symptom Score (IPSS) system of seven questions. However, the NIH-CPSI was nominated as the standard of choice for clinical trials occurring after 1999, as presented at the Annual Meeting of the American Urological Association in Dallas, Tex., in May of 1999.

It is estimated that, conventionally, physicians cannot offer about 95% of their patients who do not have a definite microbiologic etiology an evidence-based therapeutic plan. See Nickel et al., *Research Guidelines for Chronic Prostatitis, supra*, p. 229.

Various treatment protocols have been used to attempt to treat prostatitis. While Type I may be managed successfully treat prostatitis with wide spectrum antibiotics, patients having Type II and III prostatitis have had lesser degrees of response success when treated with antibiotics. Other treatment regimes include other drugs such as alpha-blocker therapy (for obstructive voiding), and anti-inflammatory agents. In addition, or alternatively, the physician may suggest lifestyle changes such as diet (such as the reduction of the intake of caffeine), exercise, sexual activity, and/or supportive psychotherapy or "coping mechanisms".

Other treatment protocols suggested include repetitive prostate massage via the rectum as performed by the patient or assisted by another (such as 2–3 times per week), phytotherapy, transurethral microwave thermo (heat) therapy, or even radical transurethral resection of the prostate, radical open prostatectomy, and bladder neck surgery. *See Prostatitis: Myths and Realities, supra*, p. 365; and *Special Report on Prostatitis Initiatives and Future Research*; Rev. Urol. 2000; 2(3):158–166 (Summer 2000) (presenting, at page 9, various recommended therapies for research in the highlights of the second International Prostatitis Collaborative Network Meeting, November 3–5, Bethesda, Md.). Unfortunately, as succinctly stated by one author, "[t] he reality of prostatitis treatment is that it results in a dismal cure rate and an unacceptably high relapse or recurrence rate." Id.

As noted above, one type of therapy proposed to treat this condition is transurethral microwave thermo (heat) therapy. See, e.g., Choi et al., *Clinical experience with transurethral microwave thermotherapy for chronic non-bacterial prostatitis and prostatodynia*, Jnl. of Endourology, Vol. 8, pp. 61–64 (1994); Montorsi et al., *Is there a role for transrectal microwave hyperthermia of the prostate in the treatment of a bacterial prostatitis and prostatodynia?* Prostate, Vol. 22, pp. 139–146, (1993); Nickel et al., *Transurethral microwave thermotherapy of nonbacterial prostatitis and prostadynia; initial experience*, Urology, Vol. 44, pp. 458–460 (1994); and Nickel et al., *Transurethral microwave thermotherapy for nonbacterial prostatitis: a randomized double-blind sham controlled study using new prostatitis specific assessment questionnaires*, Jnl. of Urology, Vol. 155, pp. 1950–1955 (1996). The transurethral microwave therapy may be delivered such that the prostatic tissue is non-uniformly exposed to the heat from the microwave energy. In addition, the use of microwave energy in the prostate may also unduly expose non-targeted tissue to the microwave energy. Further, some of the proposed microwave treatment regimes use numerous treatments, such as six treatments over a 6-week period, and success with such treatment remains uncertain. Others have proposed a transurethral needle ablation (TUNA) of the prostate for treating non-bacterial chronic prostatitis. See e.g., Giannakopoulos, et al., *Chronic Nonbacterial Prostatitis and TUNA®: 5 Years Clinical Experience*, European Eurology, 37 Supplement, p. 46 (March 2000). Still others have evaluated RF treatments. See Nickel, et al., *Transurethral radio frequency hot balloon thermal therapy in chronic nonbacterial prostatitis*, Techniques in Urology, Vol. 4, pp. 128–130 (1998).

In view of the above, there remains a need to provide improved and/or alternative treatments for chronic prostatitis.

SUMMARY OF THE INVENTION

The present invention provides minimally invasive methods and systems and related computer program products for treating prostatitis by internally massaging a portion of the prostate. The internal massage can be carried out by repetitively outwardly expanding and then contracting an expandable treatment balloon held on the perimeter of a flexible translumenal catheter positioned in the prostatic urethra In certain embodiments, the internal massage is directed to the portion of the prostate tissue located in the prostatic urethra (adjacent the bladder neck and above the verumontanum).

In certain embodiments, the massage can be concurrently performed with a thermal treatment. For example, heated fluid can be directed to the expandable treatment balloon to cause it to expand to contact targeted prostatic tissue with a desired expanded contact force (the balloon can be configured to circulate heated fluid therethrough). The heated fluid can be directed into the expandable treatment balloon so that the fluid pressure therein is altered (increased and decreased or pulsed) to repetitively change the contact force or pressure (increased and decreased) with which the treatment balloon contacts the proximate tissue to perform an "internal massage" on the interior passage of the prostatic urethra. The thermal treatment can be concurrently carried out because the heated fluid in the balloon is thermally transmitted to the localized tissue as the balloon expands and contracts (to conductively emit heat thereto). In certain embodiments, the thermal treatment and massage can be administered such that it is applied in a relatively uniform manner about the entire circumference of the inner wall of the prostatic urethra.

In other embodiments, the thermal therapy can be administered before and/or after the internal massage. In still other embodiments, the internal massage can be administered concurrently with the thermal therapy as well as before and/or after initiation of same.

In certain embodiments, the balloon pressure, massage force and/or the repetition rate of the expansion and contraction may be altered to the comfort level of the particular patient undergoing the treatment (typically the therapy can be carried out without general anesthesia and only a topical anesthetic). For example, the balloon pressure may be increased to increase the massage force over time as the tissue is heated and the prostatic tissue becomes more yielding or the patient less sensitive to the force in the prostatic urethra. The concurrent combination of pressure and heat (thermal massage therapy) may provide increased therapeutic responsiveness over thermotherapies alone.

In certain embodiments, a pulstatile flow (such as about 1–20 pulses per second or more, and/or 1–12 pulses/second, and typically about 1–5 pulses per second) can be used to alter the delivered massage force to repetitively expand and contract the treatment balloon. In addition, in certain embodiments, particularly those employing closed loop circulating systems, the magnitude of the massage force can be increased (or decreased) over the treatment period, by adjusting the flow rate or volume of the fluid in the system and, thus, the fluid pressure in (the degree of expansion of) the treatment balloon. In operation, the pressure in the balloon can be about 0.5–1.5 atm.

The thermal massage treatment period can extend from about 20 min to about 60 min (or longer) and the fluid can be heated, but controlled, so that the prostatic temperature is exposed to predetermined temperatures for selected time periods. The duration of the treatment may not include the initial time to reach the desired treatment temperature (or the time to decrease therefrom post-treatment). For example, heating the fluid to about 40–47° C. such that the prostatic tissue is exposed to non-ablation or low-level ablation temperatures for a major portion (or all) of the treatment session. In other embodiments, the fluid can be heated to an elevated level (about 50–62° C. for an initial portion of the treatment) and then reduced for the remainder of the treatment session to between about 40–47° C., and typically to about 45–47° C.

In certain embodiments, such as for treating non-bacterial chronic prostatitis, the procedure can be carried out to heat fluid to about 47° C. for about 45 minutes.

In other embodiments, prior to initiation of the thermal treatment, or as an alternative to thermal treatment using elevated temperatures (i.e. above about 40° C.), the internal massage can be administered alone by using cooled, ambient, or a low level heated medium such as water or other biocompatible substance to cause the treatment balloon to expand. In addition, the internal massage can be used while a therapeutic agent is delivered (the drug or therapeutic agent), or can be mixed with a fluid or liquid to provide a flowable inflation medium and configured to permeate the treatment balloon during the massage to facilitate migration into the tissue (to facilitate the depth penetration into the prostate) or can be fluidly directed via drug delivery ports at desired locations in the catheter. In certain embodiments, the therapeutic agent can be formulated as an aqueous mixture which is flowable so as to be able to be pumped from a location outside the body via the catheter to the treatment balloon. In other embodiments, the therapeutic agent can be introduced at a port separate from the treatment balloon (such as above or below the treatment balloon). Alternatively, the therapeutic agent may be applied as a coating on the external surface of the catheter or treatment balloon which is released during treatment (leaches out or dissolved or released based on the moisture or heat in situ so as to be absorbed into the adjacent tissue).

In certain embodiments, a single treatment session may be sufficient to treat the condition while in others a plurality of successive treatments (such as two, three, or more) may be performed over a treatment window (such as over 1 week, 1 month or 1 quarter of a calendar year). In other embodiments, an annual single treatment session or successive treatment sessions may be desired to maintain desired results. In particular embodiments, the treatments can be carried out to heat the liquid in the treatment catheter to between about 45–47° C. and deliver a plurality of treatments over a desired treatment interval. For example, the thermal therapy can be two 30–60 minute treatments carried out within two to three weeks of each other or three 30–60 treatments carried out spread out over about five-eight weeks, measured from the earliest to the latest session in the series.

The combination thermal therapy with an internal massage may also be combined with other desired treatment regimens such as lifestyle changes, exercise, and/or drug or food supplements as will be discussed further below.

In addition, in certain embodiments, because prostatitis may be more treatable when cells are more susceptible (at various points in the cell cycle such as at proliferation or cell division), a first thermal massage therapy can be delivered to influence the cell cycle and then a delay and a second thermal massage therapy can be delivered (when there is a likelihood that the cells may be susceptible to kill, such as, for example, at 8–72, or 15–48 hours from the first treatment). The first treatment may be of a different duration and/or different temperature(s) or combination of temperatures than the second treatment.

Similarly, the thermal massage treatment may be administered concurrently with or after or before a radiation treatment (or chemotherapy) to enhance the likelihood of success.

In certain embodiments, the invention is directed to a method for treating prostatitis, comprising: (a) positioning a transurethral catheter with a treatment balloon mounted thereon in the prostatic urethra of a subject; (b) expanding the treatment balloon after the positioning step so that the expanded treatment balloon contacts prostatic tissue; (c) internally massaging the prostate by altering the pressure in the expanded treatment balloon such that the expanded treatment balloon repetitively laterally or outwardly expands and contracts a desired distance in the prostatic urethra; and (d) concurrently heating the prostatic urethra during the massaging step to thereby treat the subject for prostatitis.

In still other embodiments, the invention is directed to methods for treating prostatitis in a subject, comprising: (a) inserting a catheter with at least one expandable treatment balloon thereon into the urethra of a subject, the treatment balloon positioned to extend outwardly about the perimeter of a portion of the catheter; (b) heating fluid to a desired temperature; (c) directing the heated fluid such that it travels captured through the catheter to the at least one expandable treatment balloon; (d) inflating the at least one treatment balloon responsive to the directing step, wherein, in position, the expanded treatment balloon takes on a radially expanded substantially cylindrical configuration and circumferentially contacts targeted tissue in the prostatic urethra; (e) internally massaging a portion of the prostatic urethra by repetitively altering the fluid pressure in the treatment balloon causing the treatment balloon to repetitively expand and contract a desired distance in response thereto; and (f) exposing a portion of the prostate adjacent the prostatic urethra to a thermal treatment based on steps (c) and (d) concurrently with the massaging step by heating a targeted region in the prostatic urethra to a temperature of between about 40–47° C. for a desired treatment time of at least 20 minutes to thereby perform a thermal massage of the prostate.

In still other embodiments, the invention is directed to a set of prostatitis treatment catheters having expandable treatment balloons configured to thermally massage a selected portion of the prostate. Each of the treatment balloons are configured on a flexible catheter sized and configured to be inserted into the male urethra, wherein said treatment balloons are sized in desired increments from about 0.5 cm to 1.5 cm such that, in operation, a selected treatment balloon resides above the verumontanum of the subject in the prostatic urethra. The treatment balloons may have a bladder anchoring balloon or other anchoring means thereon. In certain embodiments, the treatment balloon may be extended to heat the bladder neck, or a bladder-anchoring balloon may be used in fluid communication with the treatment balloon so as to be able to thermally treat same in position.

In certain embodiments, the present invention provides computer program products for controlling an internally delivered thermal massage treatment for prostatitis. The thermal massage treatment is typically provided by a closed loop system having a heater, a pump, and a trans-lumenal catheter-configured and sized to be inserted through the male urethra and having an outwardly expandable treatment balloon thereon. The treatment balloon is configured, in operation, to repetitively expand and contract to provide a massage to the tissue located proximate thereto while the catheter circulates heated fluid via the expandable treatment balloon. The computer program product comprising: (a) computer readable program code for controlling the temperature of fluid circulating in the catheter so that the temperature entering the catheter to travel to the expanded treatment balloon is between about 40–50° C. (or that the temperature at the external surface of the treatment balloon when measured ex vivo is between about 43–47° C.); and (b) computer readable program code for timing the duration of the thermal massage treatment so that the treatment lasts from about 20 minutes to 1 hour.

The foregoing and other objects and aspects of the present invention are explained in detail in the specification set forth below.

BRIEF DESCRIPTION OF THE DRAWINGS

FIG. 8 is a chart illustrating the results of a prostatitis treatment study using embodiments of the present invention.

DESCRIPTION OF EMBODIMENTS OF THE INVENTION

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, certain components, features or layers may be exaggerated for clarity. In the block diagrams or flow charts, broken lines indicate optional features or steps.

Figure 1A:
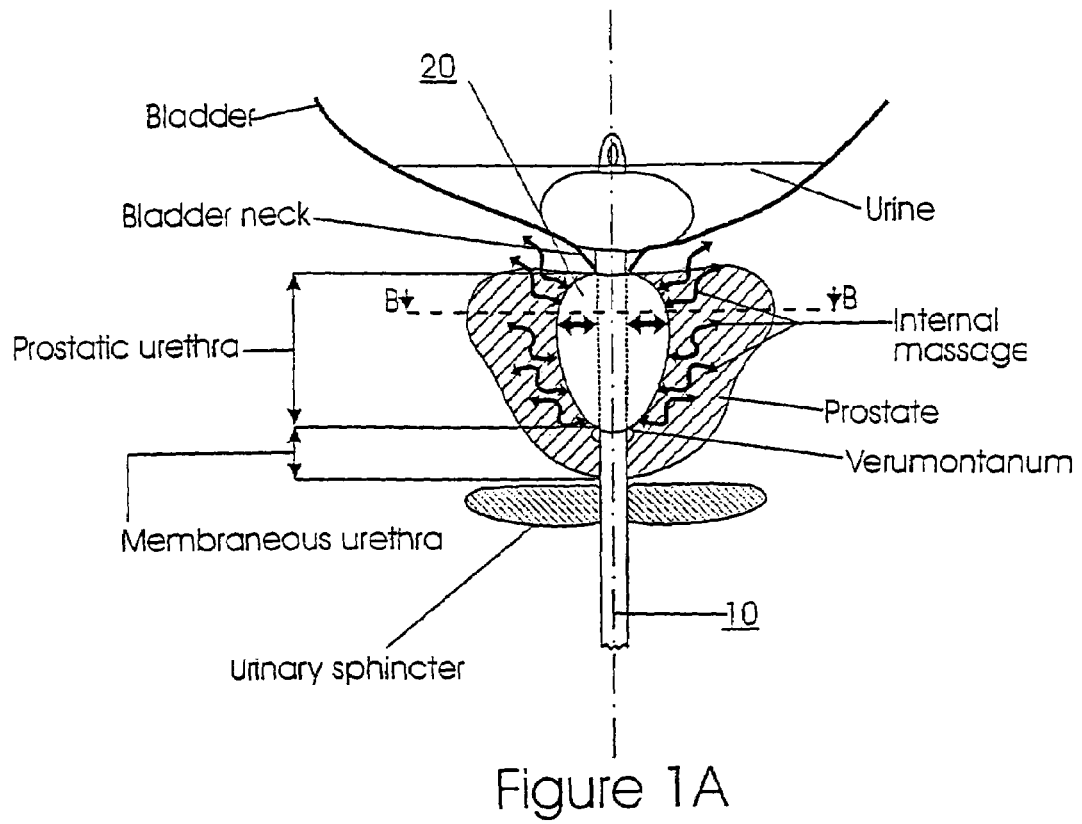
FIG. 1A is a schematic section view illustrating a catheter with an expandable treatment balloon in position in the prostatic urethra according to embodiments of the present invention.

The present invention is directed at methods and devices for treating diseases of the prostate and may be particularly suitable for treating chronic prostatitis (such as Type II, III or IV, and more particularly the Type III or IV). The present invention may also be suitable for treating prostatodynia. FIG. 1A illustrates a transluminal elongated catheter 10 which may be inserted into the prostatic urethra via the penile meatus and through the male urethra. The catheter can be a flexible catheter so as to be able to be inserted into position in manner which reduces the likelihood of discomfort (following or bending to the shape of the urethra during insertion). See, e.g., U.S. Pat. Nos 5,257,977, 5,549,559, and 5,084,044; and U.S. Provisional Patent Application Ser. Nos. 60/248,109, and 60/288,774, the contents of these documents are hereby incorporated by reference as if recited in full herein.

As shown, the catheter 10 includes at least one treatment balloon 20 positioned on an outer perimeter thereof. The treatment balloon 20 is outwardly expandable, and in position is configured and sized to contact localized tissue in the prostatic urethra Although shown throughout as a single treatment balloon positioned on a distal portion of the catheter, other configurations can also be employed. For example, the internal massage can be administered using a plurality of circumferentially spaced balloons or axially spaced balloons (not shown).

In operation, the treatment balloon 20 is configured to repetitively outwardly expand and then contract a desired distance (illustrated by the bidirectional lateral or horizontal arrows in FIG. 1A). In certain embodiments, the treatment balloon 20 is expanded so as to remain in contact with the localized tissue (or wall of the lumen) during both the expansion and contraction.

Figure 1B:
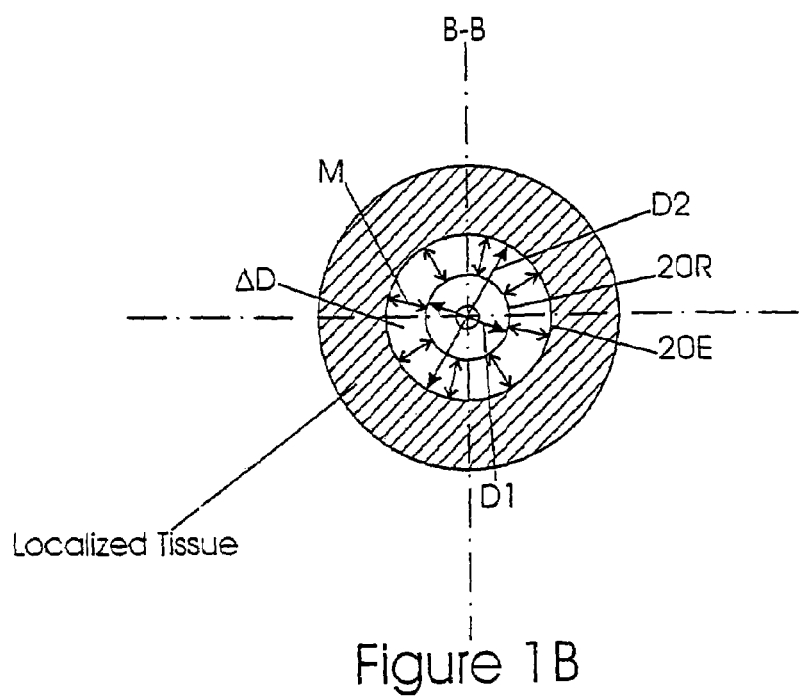
FIG. 1B is an enlarged top view of the catheter shown in FIG. 1A, illustrating the expandable balloon taking on expanded and contracted shapes according to the arrows illustrated in FIG. 1A.

As shown in FIG. 1B, in these embodiments, the treatment balloon 20 partially contracts to a smaller cross sectional width (shown as diameter D1) to ease the massage or contact force (or pressure) applied to the prostate in comparison to the increased force or pressure applied by a larger expanded shape (corresponding to the larger cross-sectional width, shown as "D2"). Thus, the "Δp" or change in massage pressure results from the change in the expansion of the treatment balloon "ΔD".

In certain embodiments, in situ, the treatment balloon 20 may not actually change its shape to the same extent when positioned inside the body as compared to when it is outside the human body of the subject. That is, the expansion movement of the balloon may be inhibited or blocked by the lumen of the prostate (and/or the resiliency of the underlying prostatic tissue). However, when operated outside the body, the treatment balloon will either visibly alter its shape and/or provide a pulsatile feeling when held encased in the palm of a person or in a measurement apparatus for recording pressure/force. During the internal massage the prostatic tissue may yield (become more elastic), allowing the balloon 20 to increase in size during the internal massage. Alternatively, or in addition, the balloon may be intentionally further expanded to provide an increased massage force or pressure. For the latter, the balloon 20 may substantially retain its pre-increased force or pressure configuration (as it is encased by the density and shape of the adjacent prostatic tissue) but still provide the increased massage force to the adjacent tissue (to promote penetration depth).

As shown in FIG. 1A, the treatment balloon 20 can be configured so that it can apply a substantially constant circumferentially distributed massage (the circumferentially distributed massage is represented by the bi-directional arrows about the outer surface of the balloon) over at least a portion of, and preferably a major length of, the prostatic urethra. This can provide a substantially uniform distribution of a (thermal) massage around the urethra to increase the likelihood that the treatment will have sufficient penetration so as to positively impact the prostate capsule. The balloon 20 can be inflated with any suitable (preferably biocompatible) inflation medium. A valve can be positioned in fluid communication with the balloon and used to direct the inflation medium to inflate and/or deflate (expand/contract) the treatment balloon. In certain embodiments, the valve can be automated to be digitally controlled to provide a relative quick massage cycle (such as about 1–12 cycles or pulses every second) or slower massage cycle (20–60 pulses per minute); the rate and force of the massage can be adjusted during the treatment as will be discussed further below.

In certain embodiments, the fluid may be circulated to cause the balloon 20 to perform the internal massage. This fluid may be a biocompatible fluid such as water or an aqueous formulation. The fluid may be cooled, or presented at ambient or slightly elevated temperatures ("slightly elevated" means heated above ambient such as to body temperature but below about 40° C.). In other embodiments, the fluid may be heated to elevated temperatures (such as to temperatures above 40° C.), the latter will be discussed further below. The treatment temperature may be that temperature associated with the circulating fluid as it enters the catheter, or may be the temperature at the external surface of the treatment balloon when measured ex vivo.

In addition, fluid circulated at a non-elevated temperature may be used to perform the massage (or an initial portion of the massage) to relax the local tissue prior to, after, or concurrent with applying an alternative therapy type. The alternative therapy can be one, or a combination of, an oral (systemically delivered) medicament or therapeutic agent, locally delivered therapeutic agent, or other therapy type such as radiation, chemotherapy, and thermal therapy.

The term "therapeutic agent" includes medicines, food supplements, or bioactive substances or formulations used to treat prostatitis or its symptoms (delivered either systemically or locally during or as an adjunct to the massage therapy), including over the counter or prescription pharmaceutical products, vitamins or food, beta radiation, and the like, examples of which will be discussed further below.

Figure 2:
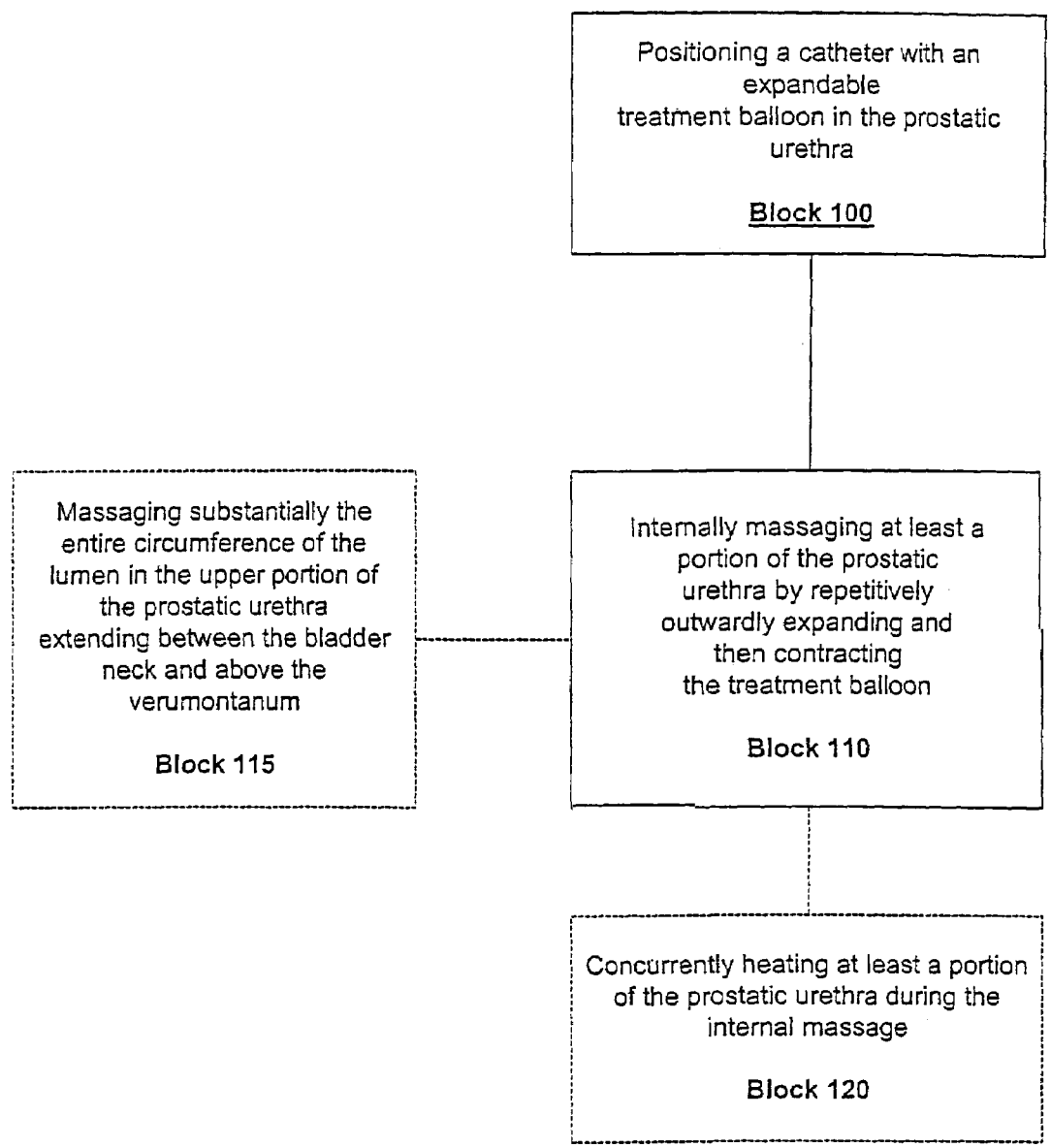
FIG. 2 is a block diagram of a method of treating prostatitis according to embodiments of the present invention.

Turning now to FIG. 2, prostatitis can be treated by inserting or positioning a catheter with an expandable treatment balloon in the prostatic urethra (block 100) and internally massaging at least a portion of the prostatic urethra by repetitively outwardly expanding and contracting the treatment balloon (block 110). The method can be carried out so that substantially the entire perimeter of the lumen adjacent the treatment balloon (shown as circumferentially administered) is massaged, preferably substantially the entire region of the prostatic urethra (extending between the bladder neck and the verumontanum) (block 115). In certain embodiments, the massage is performed before, after, and/or with administration of a thermal therapy. In certain embodiments, the method includes concurrently heating at least a portion of the prostatic urethra during the internal massage (block 120) to deliver a thermal massage therapy.

The heat can be supplied by any desired heating source including RF, microwave, laser, and the like. For example, using microwave and RF energy to heat the tissue concurrently with repetitively expanding and contracting the treatment balloon a desired distance as it resides in the prostatic urethra to provide the internal massage therapy.

In certain embodiments, the heat or thermal therapy is supplied by heating fluid external of the body of the subject and directing it so that it travels captured in the catheter to the treatment balloon. Preferably the system and the balloon are configured to continuously circulate heated fluid to a regulated desired thermal treatment temperature; times and temperatures for preferred embodiments will be discussed further below. As such, the catheter can have increased insulation regions located about the shaft below the treatment balloon 20 to insulate the non-targeted tissue as the heated fluid travels to the remote treatment site.

In certain embodiments, the massage (intensity or frequency) can be altered during the treatment. In closed loop circulating systems, the magnitude of the massage force or pressure can be increased (or decreased) over the treatment period, by adjusting the flow rate or volume (or pressure) of the fluid in the system and, thus, the fluid pressure in (the degree of expansion of) the treatment balloon. See e.g., U.S. patent application Ser. No. 09/433,952 and U.S. Pat. No. 5,549,559, the contents of which are hereby incorporated by reference as if recited in full herein, for descriptions of a suitable closed loop circulating fluid system. Fluid circulating WIT™ catheters with expandable treatment balloons are available from ArgoMed, Inc., in Cary, N.C. The pressure in the treatment balloon (which corresponds to the pressure in the closed loop system) may be from about 0.5–1.5 atm, and typically at least about 1 atm during at least a portion of the treatment to increase the pulsation force presented to the localized tissue.

Figure 3:
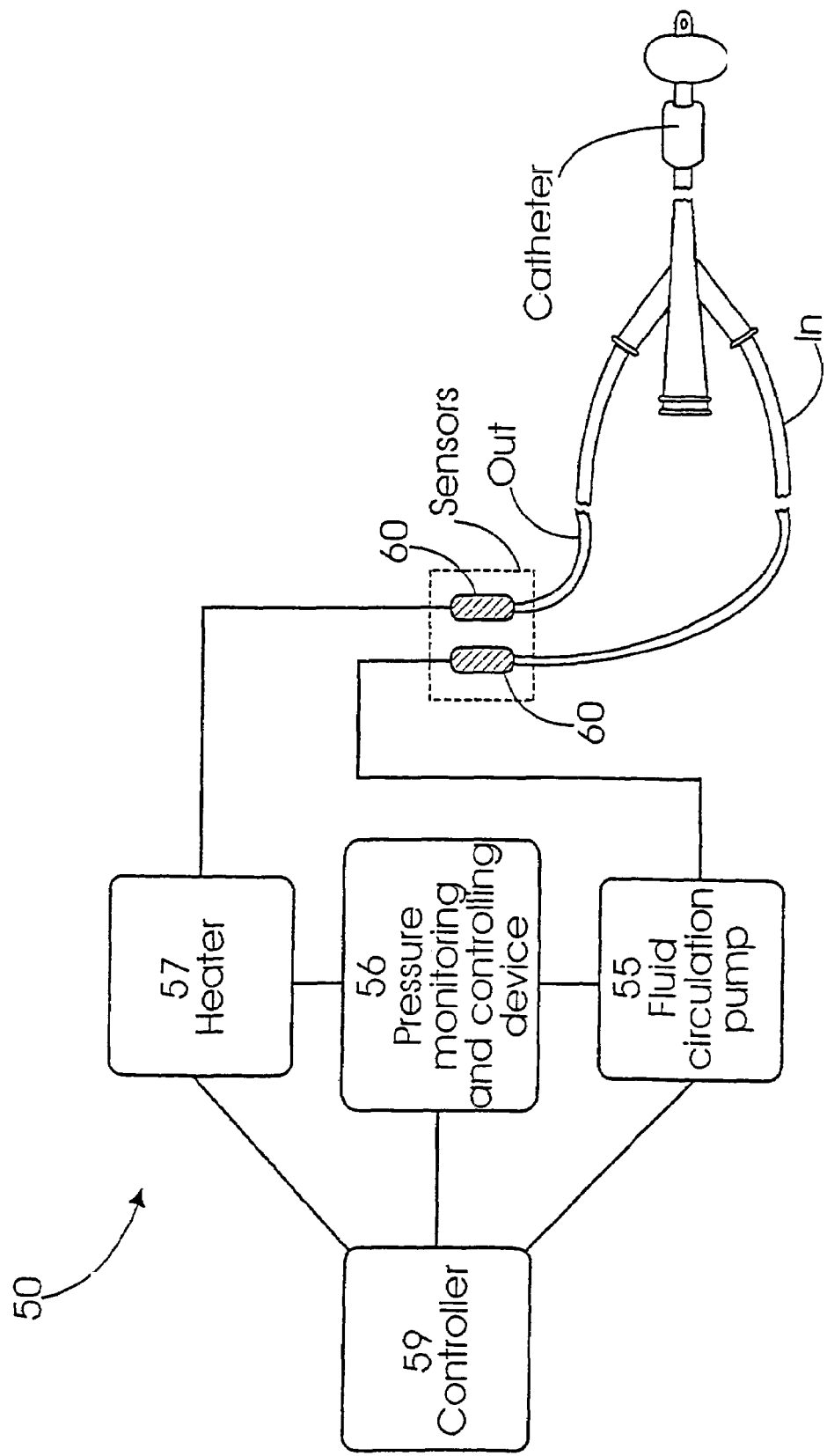
FIG. 3 is a schematic illustration of a closed loop system according to embodiments of the present invention.

FIG. 3 illustrates one embodiment of a closed loop system 50 which can be used to heat fluid which is then directed into the catheter to cause the treatment balloon to expand and also to apply a thermal therapy to the localized tissue in the prostatic urethra. As shown, the closed loop system 50 includes a fluid circulation pump 55, a pressure monitoring and controlling device 56, a heater 57, a controller 59, and temperature sensors 60, all operably associated with the catheter 20. The system can be configured as a low volume system (circulating from between about 10–75 ml of fluid). A suitable closed loop system known as the Thermoflex® System is available from ArgoMed, Inc. in Cary, N.C.

In certain embodiments, the internal massage can be provided by using a peristaltic pump to generate pulsatile fluid flow. A three roller pump may be configured to operate with between about 300–750 rotations per minute while a two roller pump may be configured to operate with between about 200–500 rotations per minute, each can operate so as to provide a corresponding number of pulses to the treatment balloon. Suitable pump heads are available from Watson Marlow Inc., of Wilmington, Mass., and Bamant Co., of Barrington, Ill. Of course, other methods for expanding and contracting a treatment balloon or generating the pulsatile flow can also be used as will be appreciated by those of skill in the art. In certain embodiments, the pulstatile flow can be provided so that the expansion/contraction rate at the treatment balloon is about 1–12 pulses per second or more, and typically about 1–5 pulses per second. This action can be used to alter the delivered massage force by causing the treatment balloon 20 to repetitively expand and contract during at least a portion of the treatment, and preferably during the entire treatment session.

Figure 4:
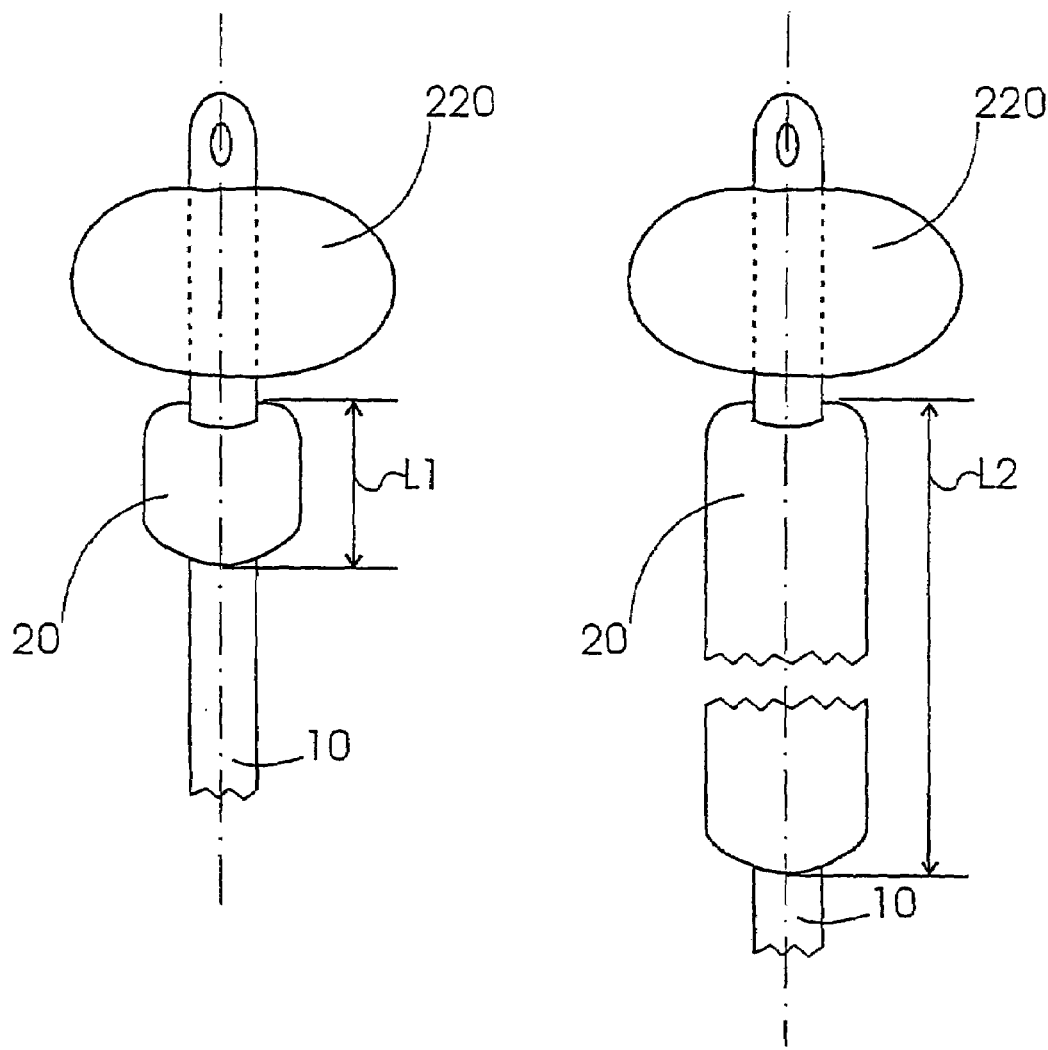
FIG. 4 is a schematic illustration of a set of treatment catheters, each having different lengths of the treatment balloon, according to embodiments of the present invention.

As shown in FIG. 1A, in certain embodiments, the treatment balloon 20 is configured with an axial length which is selected so that, in position, it resides above the verumontanum of the subject. As shown, the treatment balloon 20 extends above or proximate to the bladder neck of the subject to end at a distance which is above the verumontanum of the subject. Thus, for the treatment of prostatitis, the treatment balloons may be modified from the WIT™ catheters used in the Thermoflex® System (ArgoMed, Cary, N.C.) for treating BPH. That is, as shown in FIG. 4, the catheters 20 may be configured in an array of different treatment balloon 20 sizes and/or lengths to provide a custom fit for the subject (the length of the prostatic urethra will vary subject to subject). Further, in contrast to catheters with treatment balloons used to treat BPH (typically having lengths from about 2–6 cm), it may be desirable to configure the treatment balloons so that they have shorter axial lengths. In certain embodiments, the catheters 20 are produced in sets or in increments of from about 1–6 cm (as schematically illustrated in FIG. 4), $L_1$ representing the 1 cm length and $L_2$ representing the 6 cm length. As also shown in FIG. 4, the catheters 10 may be configured with a bladder-anchoring balloon 220 (similar to a Foley-type catheter) located above the treatment balloon 20 to secure the treatment balloon in position during the treatment. In certain embodiments, the treatment balloon 20 may be extended a length sufficient to allow an upper portion to reside adjacent the bladder neck to allow the bladder neck to be thermally treated concurrently with the prostatic urethra. Alternatively, the bladder-anchoring balloon 220 may be configured to be in fluid communication with the treatment balloon so as to be able to thermally treat the bladder neck when in position.

Figure 7:
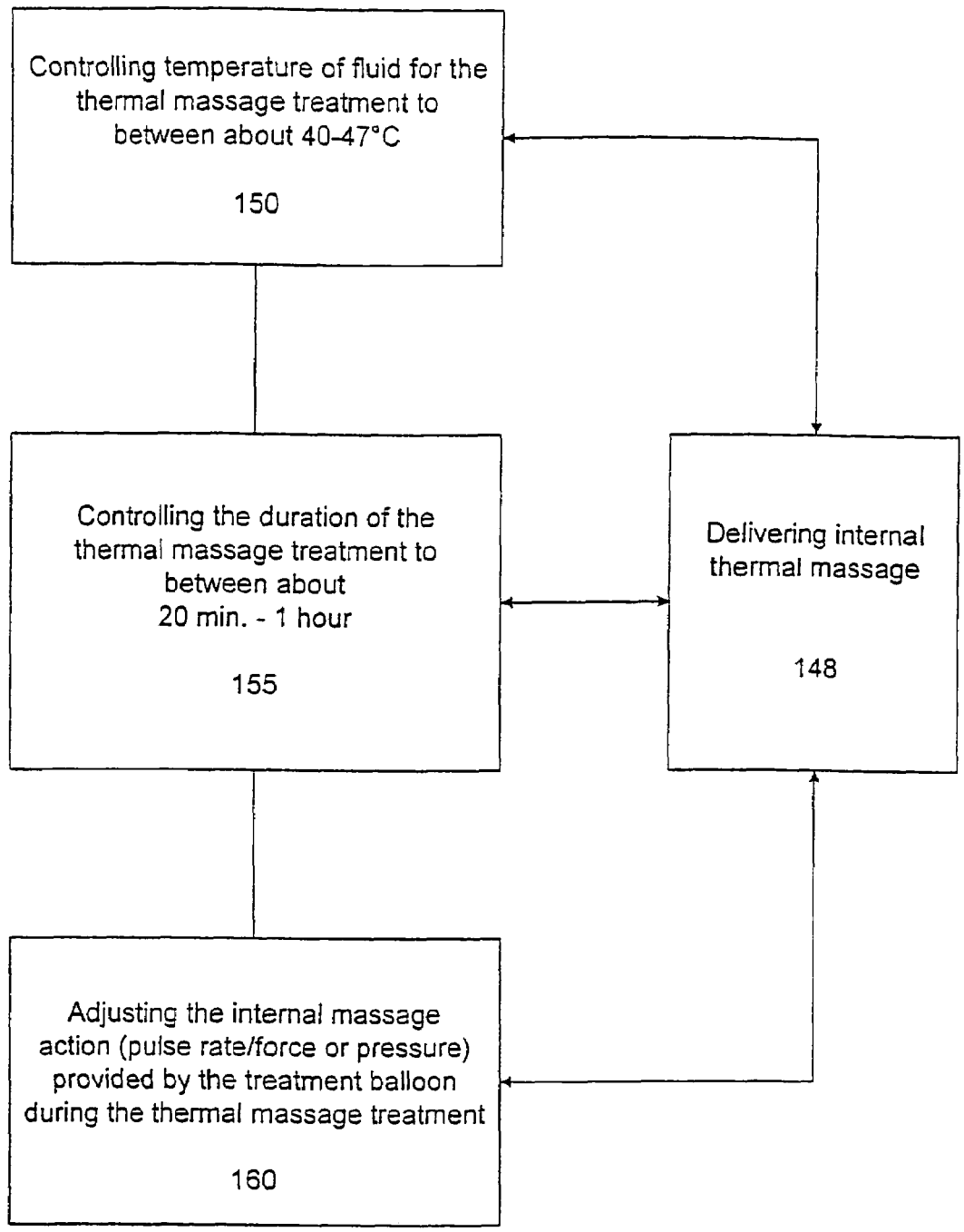
FIG. 7 is a block diagram of computer program code that can be used to control the delivery of a thermal massage according to embodiments of the present invention.
Figure 9H:
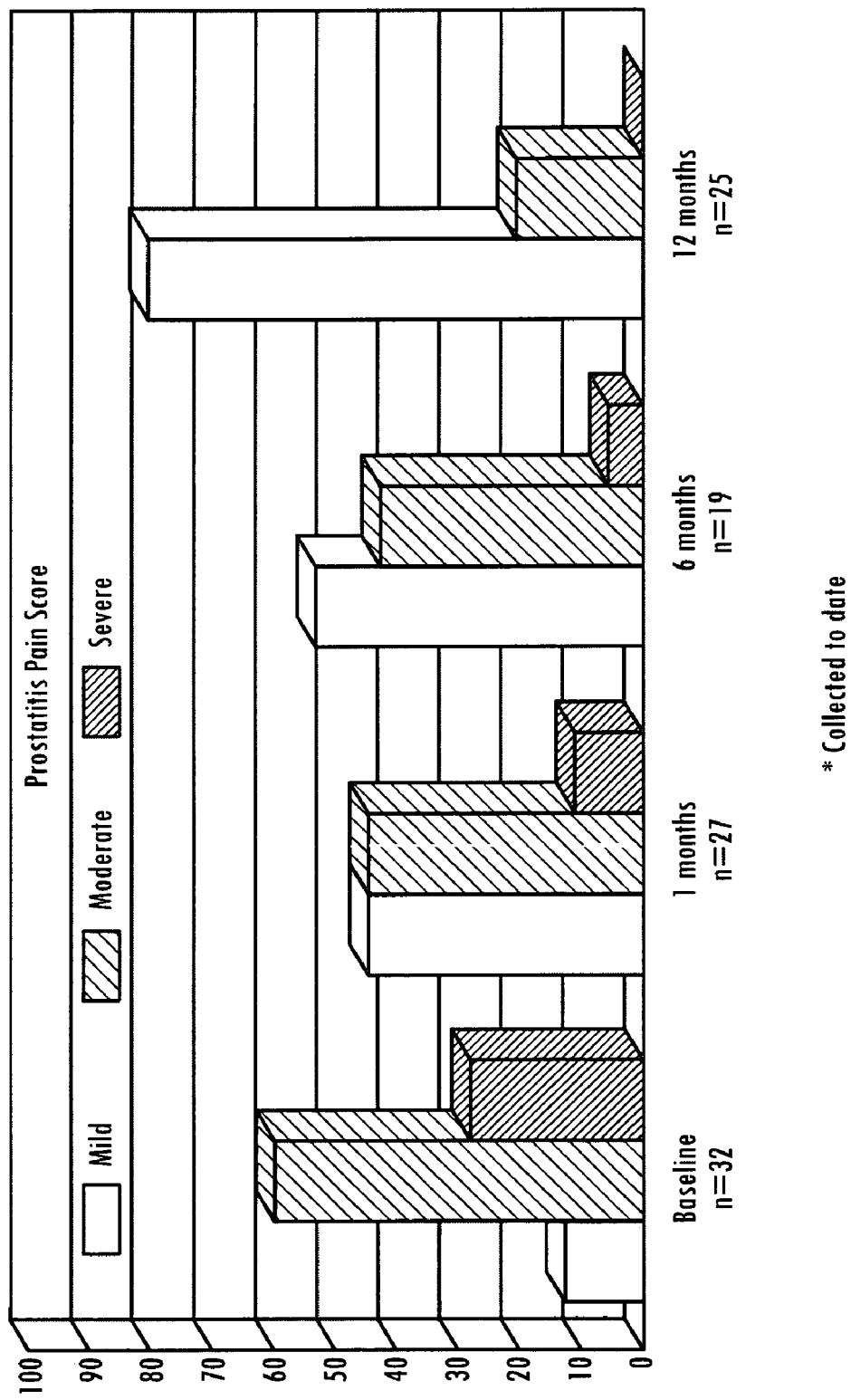
FIGS. 9A–9D are graphs illustrating the results of a chronic non-bacterial prostatitis treatment as obtained over at 1 month, 6 months and 12 months from a treatment according to embodiments of the present invention.
Figure 9B:
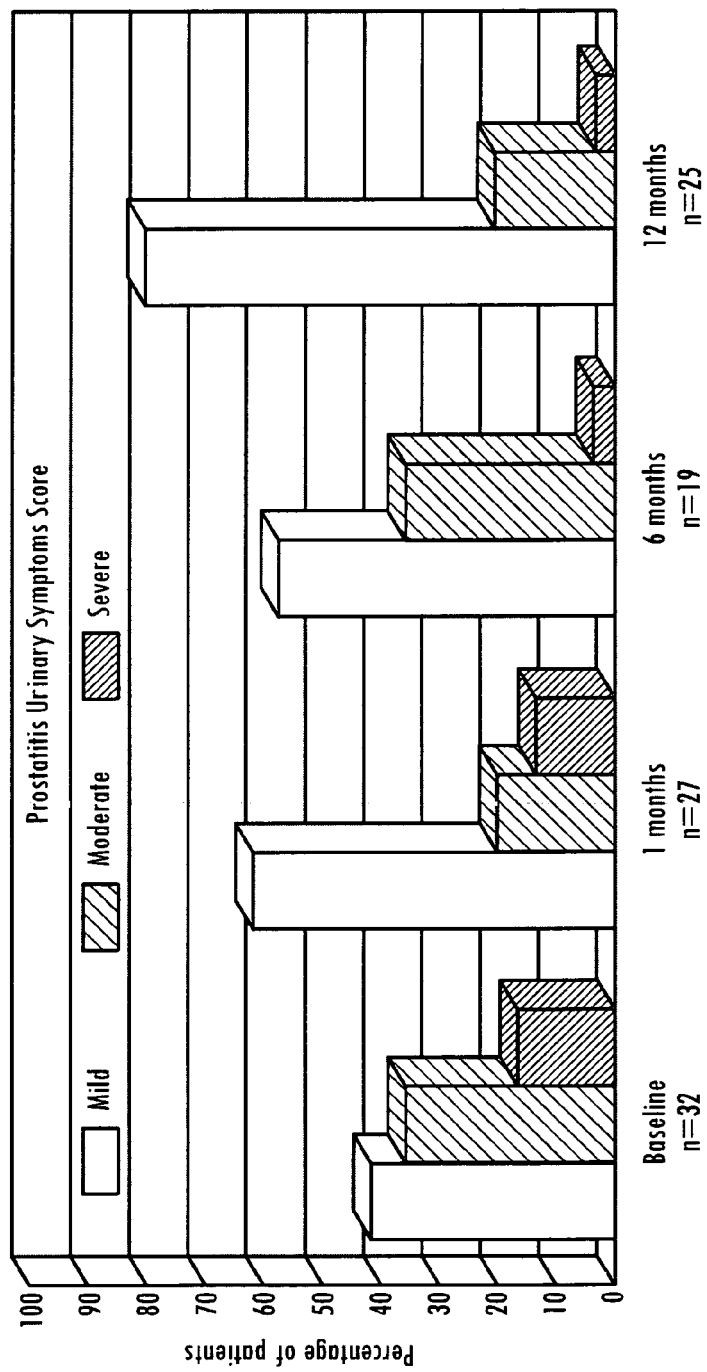
Figure 9C:
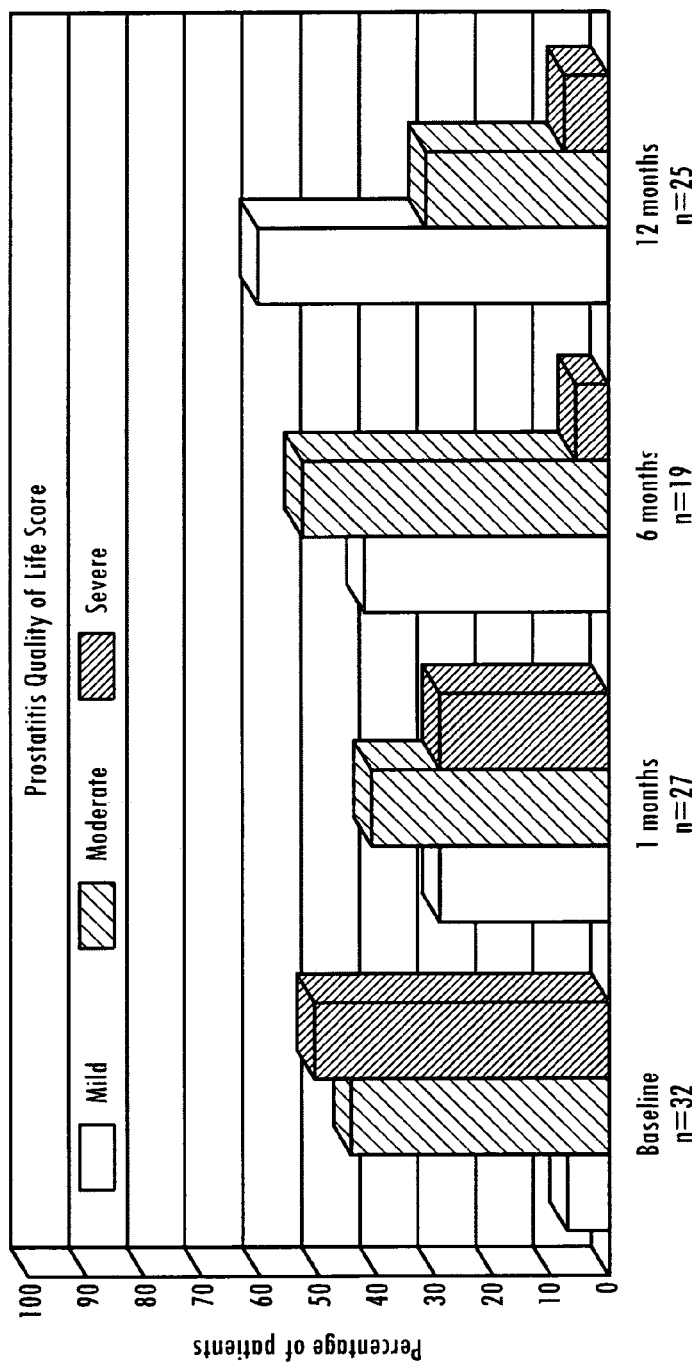
Figure 9D:
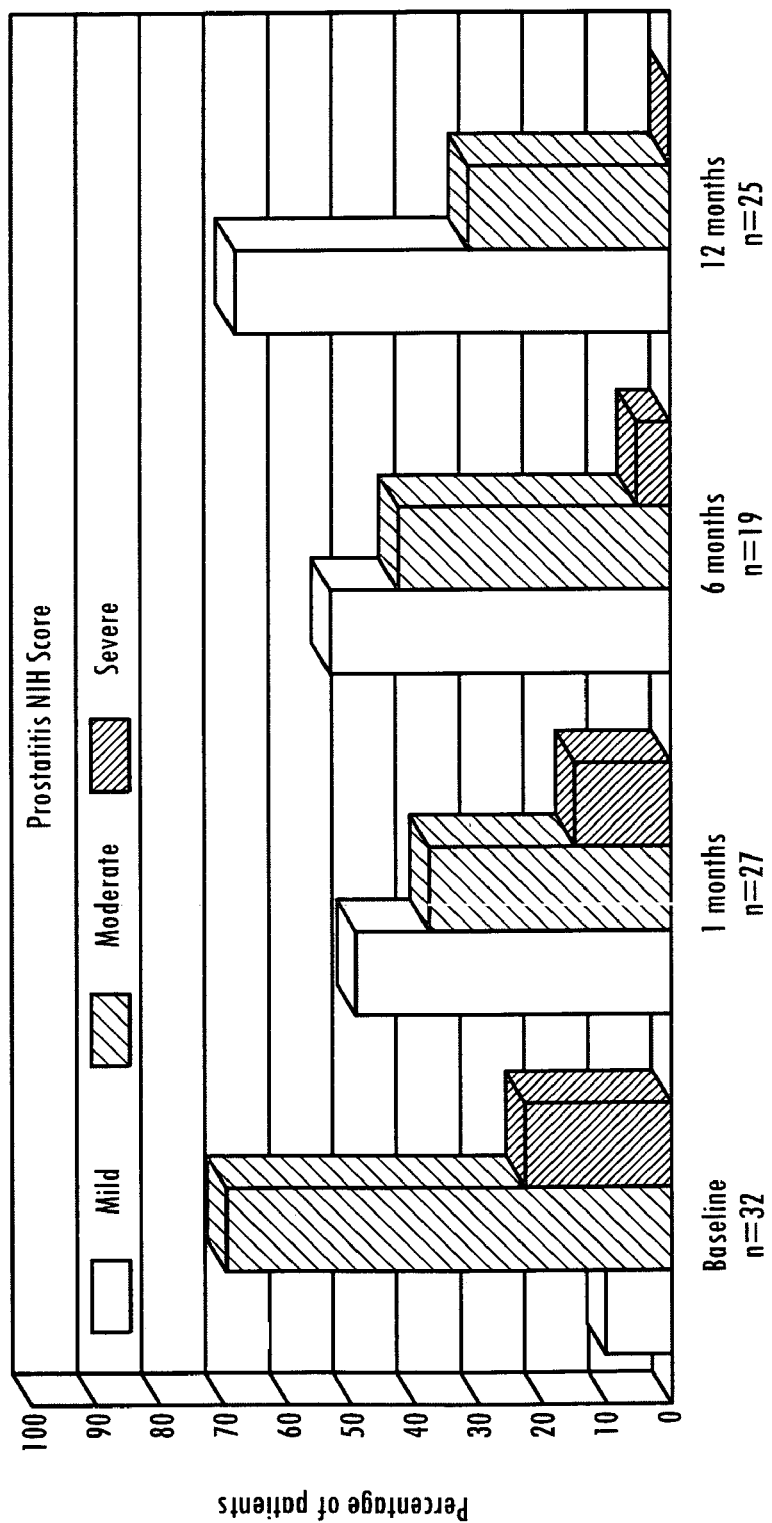

For embodiments where a thermal therapy is desired with the massage therapy, the combination treatment or "thermal massage treatment" period can extend from about 20 min to about 60 min (or longer) and the fluid can be heated in a controlled manner so that the prostatic tissue is exposed to predetermined temperatures for selected time periods. For example, for circulating systems where the fluid is heated outside the body the fluid can be heated so as to provide a treatment temperature at the treatment balloon (when measured ex vivo) to between about 40–47° C. and preferably to between about 43–47° C., and more preferably to between about 43–45° C., and still more preferably to about 45° C., such that the prostatic tissue is exposed to non-ablation or low level ablation temperatures for a major portion (or all) of the treatment session. In other embodiments, the closed loop system is configured so as to input fluid heated external of the subject to about 40–54° C. during a major portion of the thermal massage treatment as measured as the fluid enters the catheter such that the temperature at the external surface of the treatment balloon is at a desired temperature (in operation, the system may experience a temperature loss as the fluid travels to the treatment balloon and the heat is emitted through the elastic balloon). FIG. 7 illustrates operations which a computer may be programmed to cause to occur (such as by altering the action of one or more of the pump, the pressure monitoring/controlling device, or the heater).

Figure 5A:
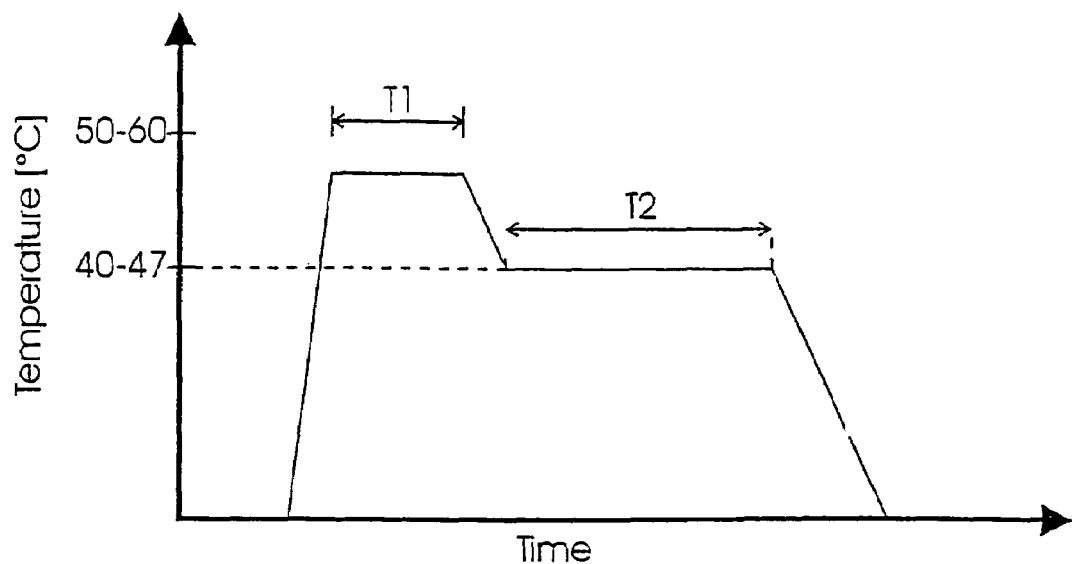
FIG. 5A is a graph of temperature versus time for thermal treatments for prostatitis according to embodiments of the present invention.

In other embodiments, as shown in FIG. 5A, the fluid can be heated to an elevated ablation level (about 50–62° C. for an initial portion of the treatment, shown as $T_1$) and then reduced to a lower temperature ($T_2$) for the remainder of the treatment session, such as to between about 40–47° C., and typically between about 43–47° C., such as 45° C. The temperature of the fluid used for the thermal treatment may be measured prior to (and proximate) its entry into the catheter when the catheter is in position in the subject (as shown by the temperature sensors in FIG. 3).

Figure 5B:
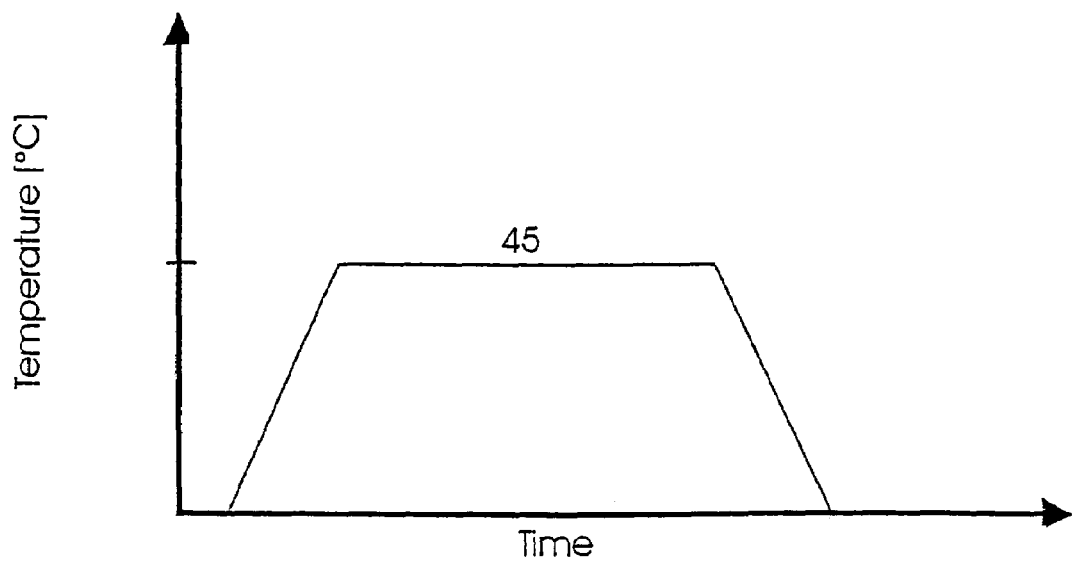
FIG. 5B is a graph of temperature versus time of a thermal treatment according to embodiments of the present invention.

FIG. 5B illustrates another embodiment of the invention. In this embodiment, the thermal massage therapy can be performed at about 45° C. for between about 20–60 minutes and typically about 30–45 minutes. It is noted that the temperature that when positioned in vivo, the tissue proximate the treatment balloon can be exposed to a reduced temperature compared to the temperature at the catheter. That is, when used in vivo, the tissue can act as a heat sink due to blood circulation, which, in turn, can decrease the temperature at which the tissue is exposed during treatment by about 5 degrees, at certain treatment temperatures, compared to the temperature of the fluid as it enters the catheter.

Figure 6:
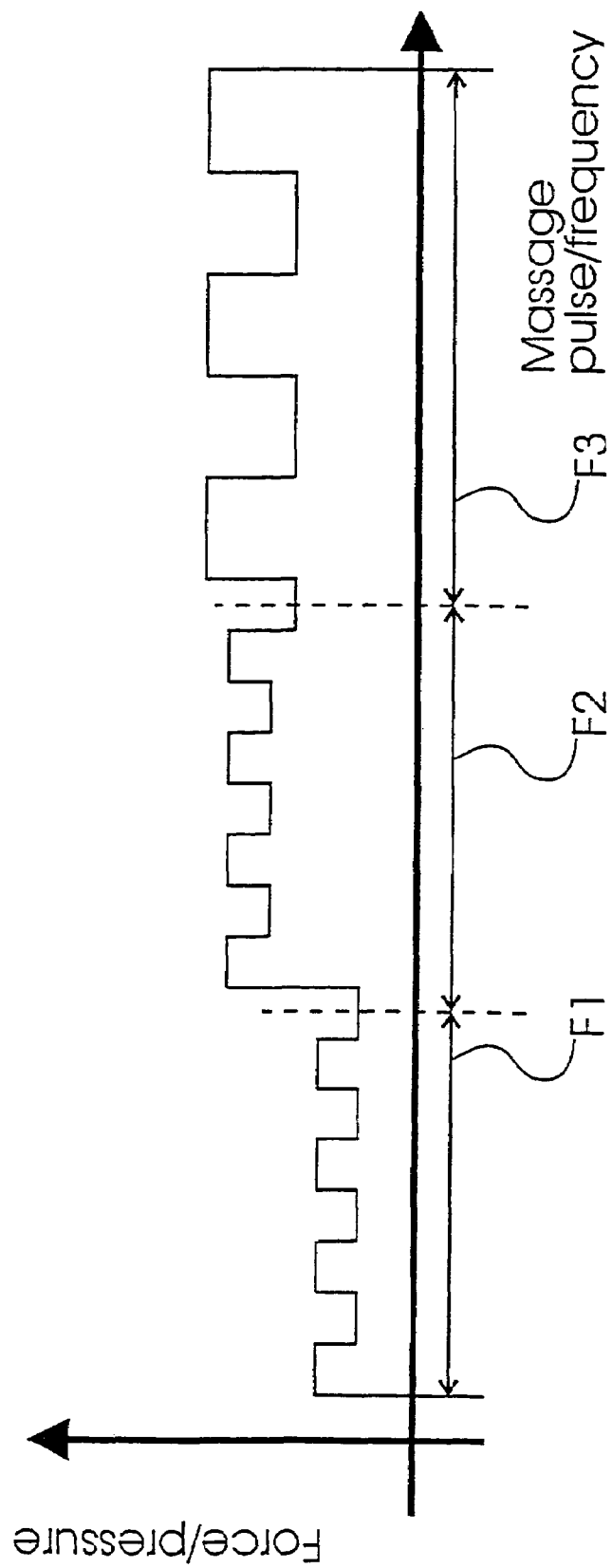
FIG. 6 is a graph of force or pressure over time that can be used for administering an internal massage to the prostate according to embodiments of the present invention.

FIG. 6 graphically illustrates that one or more of (a) the massage pressure or force or (b) the massage frequency (i.e., the pulse frequency or the number of times the balloon contracts and expands during a given unit of time) can be altered during the treatment. FIG. 6 illustrates that both the massage frequency and the force are increased relative to time periods $T_1$ and $T_2$ and then the force remains the same but the massage frequency is decreased relative to time periods $T_2$ and $T_3$.

In certain embodiments, the massage force and/or the repetition rate of the expansion and contraction may be altered on a customized level to the comfort level of the particular patient undergoing the treatment (typically the therapy is carried out without general anesthesia and only a topical anesthetic). For example, the massage force or pressure in the system and/or balloon -may be increased over time as the tissue is heated and the prostatic tissue becomes more yielding or the patient less sensitive to the force in the prostatic urethra. The concurrent combination of pressure and heat may provide increased therapeutic responsiveness over thermotherapies alone. In alternative embodiments, the thermal therapy is delivered alone and the pressure that the balloon is expanded to is adjusted in controlled increments (to inhibit undue pressures) based on the tolerance/comfort of the particular patient undergoing therapy. The pressure may be increased during the procedure as the patient becomes accustomed to the procedure.

In other embodiments, prior to initiation of the thermal treatment, or as an alternative to thermal treatment, the internal massage can be administered alone by using a low beat or cooled or ambient non-heated medium such as water or other biocompatible substance to cause the treatment balloon to expand.

In addition, the thermal or thermal massage treatment can be used while also delivering or administering a therapeutic agent or radiation. For example, a therapeutic agent can be mixed with a fluid or liquid to provide a flowable inflation medium which can be configured to permeate the treatment balloon during the massage to thereby migrate into the tissue (to facilitate the penetration therein as the prostate tissue may be more receptive to the uptake or more relaxed with the massage). The therapeutic agent may be configured to maintain its efficacy at elevated temperatures (at least between about 40–43° C.). In other embodiments the therapeutic agent can be applied as a coating on the perimeter surface of the balloon so that the tissue is exposed upon contact with the balloon during the treatment. In still other embodiments, a portion of the catheter such as the external surface of the expandable treatment balloon can be coated with a radioisotope of beta emitting isotope (such as P(32), Y(90), or Sr(90)).

Additionally, the medicament or therapeutic agent can be fluidly directed into the prostatic urethra by directing it up through a fluid lumen in the catheter and out via a drug delivery port(s) at desired locations in the catheter. In certain embodiments, the therapeutic agent can be formulated as an aqueous mixture which is flowable and heatable so as to be able to be pumped from a location outside the body via the catheter to a location inside the body proximate to the treatment balloon and used to perform the internal thermal massage therapy while also migrating to localized tissue during the treatment. The wiping action of the massaging balloon and/or the localized heat may help facilitate uptake or penetration into the localized tissue.

In certain embodiments, a single treatment session may be sufficient to treat the condition while in others a plurality of successive treatments (such as two, three, or more) may be performed over a treatment window (such as over 1 week, 1 month or 1 quarter of a calendar year). The thermal massage therapy may also be combined with other desired supplemental or adjunct treatment regimens such as lifestyle changes, exercise, and/or selected therapeutic agents or food supplements (alone, or in combination). The desired supplemental treatment may be initiated prior to, during or after the thermal massage treatment(s) and may also continue for periods of time thereafter. Examples of therapeutic agents which may be beneficial include one or more of analgesics, anti-depressants, phytotherapy therapeutics such as PEENUTS or PROSTA-Q, anti-inflammatory agents such as steroid inhibitors (such as COX-2 inhibitors like VIOXX) and PENTOSAN POLYSULFATE, non-steroid inhibitors, antibiotics, neuroleptic agents (such as ELVAIL, NEURONTIN, DOXEPIN, and MARCAINE), α-blockers (such as PHENOXIBENZAMINE), specific immunology modulators such as ENBREL (by Immunex, a drug approved by the FDA for rheumatoid arthritis, an autoimmune disease), bioflavinoids to reduce the level or oxidants in the prostatic fluid, FINASTERIDE, antioxidants, quercitan, and the like.

In addition, in certain embodiments, because prostatitis may be more treatable when cells are more susceptible (at various points in the cell cycle such as at proliferation or cell division), a first thermal massage therapy can be delivered to attempt to influence the cell cycle and then, after a suitable delay, a second thermal massage therapy can be delivered (when there is a likelihood that the cells are likely to be susceptible for kill, such as, for example, after about 8–72 hours, or within about 15–48 hours from the first treatment). In addition, the first treatment may be of a different duration and/or different temperatures) than the second treatment. That is, the first treatment may include the ablation level temperatures for a period of time as shown in FIG. 5A, while the second treatment may be carried out at the lower temperatures (such as between 40–47° C., and typically about 45° C.).

It will be understood that one or more blocks of the block diagrams and combinations of blocks in block diagram figures can be implemented or directed to be carried out by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus or associated hardware equipment to function in a particular manner diagrams.

FIG. 7 illustrates an embodiment of operations provided by the present invention control the delivery of the thermal massage therapy (block 148). The operations may be carried out by a combination of software and hardware and can include a computer code for implementing the operations. As shown, the operations include controlling the temperature of the fluid entering the catheter such that the temperature (for at least a major portion of the treatment) is between about 40–47° C. (block 150). Controlling the duration of the thermal massage treatment to between about 20 minutes to 1 hour (block 155) and computer code for adjusting the massage action (either automatically or upon clinician input) during the treatment session (block 160). In certain embodiments, the program may also include means for adjusting the treatment temperature during the session such as from ablation levels (such as 50–60° C.) during an initial portion of the treatment and then reducing it to a low level ablation temperature or non-ablation temperature for a major portion of the treatment session.

The internal thermal or thermal massage therapy provided by operations of the present invention can be a non-traumatic, minimally invasive therapy for restoring normal prostate function and/or improving the pain or quality of life of the subject. The heat generated during the thermal therapy can result in blood flow redistribution, which, in turn, may result in adhesion molecule difference and/or a difference in expression or prostate remodeling. The thermal therapy provided by the instant invention may help regulate apoptosis in the prostate that may beneficially influence lower urinary tract symptoms in men with prostatitis. Further the thermal therapy may act on the nerve endings in the inflamed prostate that may reduce the pain or improve the quality of life for the subject.

The invention will now be illustrated with reference to certain examples which are included herein for the purposes of illustration only, and which are not intended to be limiting of the invention.

EXAMPLES

FIG. 8 is a chart of a prostatitis study carried out in Europe using embodiments of the present invention. The treatment included a single session of thermal massage therapy carried out at about 47° C. (temperature at entry to catheter) for 40 minutes. Based on the present success of treatments, clinicians stated that any treatment illustrating a 50% success rate would be deemed effective. The thermal massage treatment appears to have provided a 57–67% success rate (based on 6 or 7 patients in the study (and one treatment session).

As shown, the chart includes some information about the subject including the date of birth, prostate length and size treatment balloon used. The chart includes pre-treatment (baseline) NIH CPSI (chronic prostatitis symptom index) scores for P (pain), US (urinary symptoms), and QL (quality of life). The chart illustrates the same information at corresponding one and three month follow-up times. It is noted that the QL scores showed improvements from 2–6 points for each of the patients. The majority of patients have shown significant improvements in at least two of the three index categories (P, US, or QL). Both P and US categories influence the QL score.

FIGS. 9A–9D are graphs of the percentage of patients with mild, moderate, and severe exhibited results for treatments for chronic non-bacterial prostatitis obtained on a number of patients (represented by n= at the various data collection points) and improvement percentages from baseline for pain score (FIG. 9A), urinary symptoms (FIG. 9B), quality of life scores (FIG. 9C), and NIH score (FIG. 9D) relative to a baseline score over selected measurement intervals of 1 month (from treatment), 6 months and 12 months. The treatments included a 45 minute water induced therapy treatment at 47° C. The results indicate improvement and durability at 1 year measured across all measurement scales. After the therapy, the majority of patients shifted from severe and moderate to mild symptoms. The improvements are thought to be about 54% on the NIH scale, with urinary symptoms improved by 45%, pain improved by 56%, and quality of life improved by 50%.

The foregoing is illustrative of the present invention and is not to be construed as limiting thereof Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for treating prostatitis, comprising:
   positioning a transurethral catheter with a treatment balloon mounted thereon in the prostatic urethra of a subject;
   expanding the treatment balloon after the positioning step so that the expanded treatment balloon contacts prostatic tissue;
   internally massaging the prostate by altering the pressure in the expanded treatment balloon such that the expanded treatment balloon repetitively laterally expands and contracts a desired distance in the prostatic urethra; and
   concurrently heating the prostatic urethra during said massaging step to thereby treat the subject for prostatitis.

2. A method according to claim 1, wherein said heating step comprises heating fluid external of the body of the subject to a temperature of between about 40–47° C., and wherein said method further comprises directing the heated fluid to travel in the catheter to the treatment balloon for a period of at least about 20 minutes.

3. A method according to claim 2, wherein said heating step heats the fluid to about 45° C., wherein said directing step directs the heated fluid to travel in the catheter to the treatment balloon for about 20–60 minutes.

4. A method according to claim 1, wherein said internally massaging step is carried out by circulating pulsating heated fluid in an enclosed circulating travel path.

5. A method according to claim 4, wherein the circulating travel path is defined by a closed loop system which includes the catheter, an inlet conduit and an outlet conduit in fluid communication with the catheter, and a heater, pump, and temperature sensors operably associated with the catheter, and wherein said massaging step comprises adding fluid to the closed loop system to increase the pressure in the treatment balloon at desired intervals over the duration of the treatment period.

6. A method according to claim 1, wherein the prostatic urethra is heated during said heating step to an elevated temperature of between about 50–60° C. for a portion of the treatment and then heated to a decreased temperature of between about 40–47° C. for a subsequent portion of time during the treatment.

7. A method according to claim 6, wherein said heating step comprises heating fluid external of the body of the subject and directing the heated fluid to travel in the catheter to the treatment balloon.

8. A method according to claim 7, wherein said heating step is carried out such that the prostatic urethra is exposed to the elevated temperature for a period of between about 5–10 minutes during a beginning portion of the treatment and then exposed to about 40–45° C. for about 20–50 minutes during a second portion of the treatment.

9. A method according to claim 8, wherein the pressure in the expanded balloon is increased during the second portion of the treatment.

10. A method according to claim 9, wherein the repetitive lateral expansion and contraction is carried out at a rate of about 1–5 cycles per second.

11. A method according to claim 1, wherein the expanded treatment balloon is sized and configured to reside in the prostatic urethra above the verumontanum during said heating and massaging steps.

12. A method according to claim 1, farther comprising the step of administering a therapeutic agent to the subject proximate in time to said treatment to facilitate the success of treatment.

13. A method according to claim 12, wherein said administering step is carried out at about 12–72 hours after said treatment.

14. A method according to claim 13, wherein said therapeutic agent comprises an antioxidant.

15. A method according to claim 13, wherein said therapeutic agent comprises quercetin.

16. A method according to claim 15, wherein said therapeutic agent comprises a phytotherapeutic agent.

17. A method according to claim 12, wherein said therapeutic agent comprises an anti-inflammatory agent.

18. A method according to claim 12, wherein said therapeutic agent comprises an antibiotic.

19. A method according to claim 12, wherein said therapeutic agent comprises finasteride.

20. A method according to claim 1, wherein said treatment is carried out proximate in time to administering radiation to the prostate of the subject.

21. A method for treating prostatitis in a subject, comprising:
   (a) inserting a catheter with at least one expandable treatment balloon thereon into the urethra of a subject, the treatment balloon positioned to extend outwardly about the perimeter of a portion of the catheter;
   (b) heating fluid to a desired temperature;
   (c) directing heated fluid such that it travels captured through the catheter to the at least one expandable treatment balloon;
   (d) inflating the at least one treatment balloon responsive to the directing step, wherein, in position, the inflated treatment balloon takes on a radially expanded configuration and circumferentially contacts targeted tissue in the prostatic urethra;
   (e) internally massaging a portion of the prostatic urethra by repetitively altering the fluid pressure in the treatment balloon causing the treatment balloon to repetitively expand and contract a desired distance in response thereto; and
   (f) heating a targeted region in the prostatic urethra to a temperature of between about 40–47° C. for a desired treatment time of at least 20 minutes concurrently with said massaging step thereby performing a thermal massage of the prostate.

22. A method according to claim 21, wherein said method is repeated about 18 hours to about 1 week from the first treatment.

23. A method according to claim 21, wherein said heating step heats the fluid to about 45° C. to heat prostatic tissue for about 20–60 minutes.

24. A method according to claim 21, wherein a portion of the prostatic urethra is heated during step (f) to an elevated temperature of between about 50–60° C. for a portion of the treatment and then heated to a decreased temperature of between about 40–47° C. for a subsequent portion of the treatment.

25. A method according to claim 21, wherein said internally massaging step comprises circulating pulsating heated fluid in an enclosed circulating travel path.

26. A method according to claim 24, wherein step (f) is carried out such that the prostatic urethra is exposed to the elevated temperature for about 1–10 minutes during a beginning portion of the treatment and then exposed to a reduced temperature of about 40–45° C. for about 20–50 minutes during a second portion of the treatment.

27. A method according to claim 21, further comprising increasing the massage pressure in the expanded balloon by at least about 10% during the treatment.

28. A method according to claim 21, wherein the treatment balloon is repetitively expanded and contracted at a rate of about 1–5 times per second.

29. A method according to claim 21, wherein the expanded treatment balloon is sized and configured to reside in the prostatic urethra above the verumontanum during said heating and massaging steps.

30. A method according to claim 21, further comprising the step of administering a therapeutic agent to the subject proximate in time to said thermal massage treatment to facilitate the success of treating prostatitis.

31. A method according to claim 30, wherein said administering step is carried out at about 12–72 hours after said thermal massage treatment.

32. A method according to claim 30, whereto said therapeutic agent comprises an antioxidant.

33. A method according to claim 30, wherein said therapeutic agent comprises quercetin.

34. A method according to claim 30, wherein said therapeutic agent comprises a phytotherapeutic agent.

35. A method according to claim 30, wherein said therapeutic agent comprises an anti-inflammatory agent.

36. A method according to claim 30, wherein said therapeutic agent comprises an antibiotic.

37. A method according to claim 30, wherein said therapeutic agent comprises finasteride.

38. A method according to claim 21, wherein the treatment is carried out proximate in time to administering radiation to the prostate of the subject.

39. A set of prostatitis treatment catheters having expandable treatment balloons, the treatment balloons configured on a flexible catheter sized and configured to be inserted into the male urethra, wherein said treatment balloons are sized in 0.5 cm increments from about 1 cm to 6 cm such that, in operation, a selected treatment balloon resides above the verumontanum of the subject in the prostatic urethra.

40. A set of treatment catheters according to claim 39, wherein the treatment balloons are thermal massage treatment balloons configured to repetitively laterally expand and contract over a desired treatment period and to emit heat therefrom.

41. A set of treatment catheters according to claim 39, wherein the catheters are configured to circulate heated fluid therein to cause the treatment balloon to pulsate responsive thereto.

42. A computer program product for controlling an internally delivered thermal massage treatment for prostatitis, the thermal massage treatment being provided by a closed loop system having a heater, a pump, and a trans-lumenal catheter configured and sized to be inserted through the male urethra and having an outwardly expandable treatment balloon thereon and configured, in operation, to repetitively expand and contract to provide a massage to the issue located proximate thereto while the catheter circulates heated fluid via the expandable treatment balloon, the computer program product comprising:

a computer readable storage medium having computer readable program code embodied in said medium, said computer-readable program code comprising:

computer readable program code for controlling the temperature of fluid circulating in the catheter so that the temperature of the fluid entering the catheter to travel to the expandable treatment balloon is between about 40–47° C.; and computer readable program code for timing the duration of the thermal massage treatment so that the treatment lasts from about 20 minutes to 1 hour.

43. A computer program product according to claim 42, comprising computer readable program code for adjusting the massage generated by the expandable treatment balloon during the treatment by altering one of the pumping speed or pressure in the balloon.

44. A computer readable product according to claim 42, comprising computer readable program code for adjusting the rate of the expansion and contraction of the expandable balloon to thereby adjust the massage rate provided thereby.

45. A computer program product according to claim 42, wherein the computer program code for controlling the time and temperature of the thermal massage treatment is configured so that the treatment is carried out at a temperature of about 45° C. as measured prior to its inlet into the catheter and wherein the duration of the treatment is about 30–40 minutes.

46. A computer program product according to claim 42, wherein said computer readable program code for controlling the temperature of fluid circulating in the catheter is configured so that the temperature at the expanded treatment balloon is between about 40–47° C. for a major portion of the thermal massage treatment and at a temperature elevated above this temperature range for another portion of the treatment.

47. A computer program product according to claim 46, wherein said computer readable program code for timing the duration of the thermal massage treatment comprises code for timing the major portion of the treatment to extend from about 20–50 minutes and timing the elevated portion of the treatment to be at about 1–10 minutes, wherein together the sum of each of the portions being about 21 minutes to 1 hour.

48. A computer program product according to claim 46, wherein the elevated temperature is from about 50–60° C. and the associated treatment duration is about 1–10 minutes, and wherein the computer program times the delivery of the elevated temperature such that it occurs during a beginning portion of the treatment and wherein the major portion of the treatment is carried out at a temperature of about 40–45° C. thereafter.

49. A computer program product according to claim 42, further comprising computer program code for increasing the massage pressure provided by the expanded balloon by at least about 10% during the treatment based on the input of the patient undergoing the treatment.

\* \* \* \* \*